(12) United States Patent
Chouzier et al.

(10) Patent No.: US 9,975,116 B2
(45) Date of Patent: May 22, 2018

(54) PROCESS FOR THE MANUFACTURE OF ALCOHOL AND/OR KETONE

(71) Applicant: RHODIA OPERATIONS, Paris (FR)

(72) Inventors: Sandra Chouzier, Lyons (FR); Luis Fernando Rascon Cruz, Woluwe-Saint-Lambert (BE); Bert Weckhuysen, BV Houten (NL); Sergio Mastroianni, Lyons (FR)

(73) Assignee: Rhodia Operations, Paris (FR)

( * ) Notice: Subject to any disclaimer, the term of this patent is extended or adjusted under 35 U.S.C. 154(b) by 0 days. days.

(21) Appl. No.: 15/531,114

(22) PCT Filed: Nov. 20, 2015

(86) PCT No.: PCT/EP2015/077203
§ 371 (c)(1),
(2) Date: May 26, 2017

(87) PCT Pub. No.: WO2016/083256
PCT Pub. Date: Jun. 2, 2016

(65) Prior Publication Data
US 2017/0266651 A1    Sep. 21, 2017

(30) Foreign Application Priority Data

Nov. 28, 2014    (EP) ..................... 14306924

(51) Int. Cl.
| | | |
|---|---|---|
| *B01J 37/08* | (2006.01) | |
| *B01J 37/06* | (2006.01) | |
| *B01J 37/00* | (2006.01) | |
| *B01J 23/26* | (2006.01) | |
| *B01J 27/24* | (2006.01) | |
| *C07C 45/53* | (2006.01) | |

(52) U.S. Cl.
CPC ............. *B01J 37/086* (2013.01); *B01J 23/26* (2013.01); *B01J 27/24* (2013.01); *B01J 37/0018* (2013.01); *B01J 37/06* (2013.01); *C07C 45/53* (2013.01); *C07C 2523/24* (2013.01); *C07C 2523/26* (2013.01); *C07C 2601/14* (2017.05)

(58) Field of Classification Search
CPC ............. C07C 45/53; B01J 31/00; B01J 23/26
USPC ................................................. 568/385, 798
See application file for complete search history.

(56) References Cited

U.S. PATENT DOCUMENTS

| | | | | |
|---|---|---|---|---|
| 3,927,105 | A * | 12/1975 | Brunie | .................... C07C 45/53 568/342 |
| 2003/0097025 | A1* | 5/2003 | Clark | .................. B01J 31/1633 568/385 |
| 2012/0310012 | A1 | 12/2012 | Chouzier et al. | |

FOREIGN PATENT DOCUMENTS

CN        102397794 A        4/2012

* cited by examiner

*Primary Examiner* — Sikarl A Witherspoon

(57) ABSTRACT

Process for the manufacture of at least one alcohol and/or at least one ketone, which comprises a step during which at least one organic peroxide compound is put into contact with at least one catalyst responding to formula (I) $CrN_xO_y$, Formula (I) in which x is a number varying from 0.10 to 1.00 and y is a number varying from 0.00 to 1.50, in order to produce the at least one alcohol and/or at least one ketone.

14 Claims, No Drawings

PROCESS FOR THE MANUFACTURE OF ALCOHOL AND/OR KETONE

This application is a U.S. national phase entry under 35 U.S.C. § 371 of International Application No. PCT/EP2015/077203, filed Nov. 20, 2015, which claims priority to EP14306924.3 filed on Nov. 28, 2014. The entire content of each of these applications is hereby incorporated herein by reference.

The present invention relates to a process for the manufacture of at least one alcohol and/or at least one ketone.

Certain processes for the synthesis of oxidized compounds such as acids, diacids, alcohols and ketones, use organic peroxide compounds as raw materials or as intermediate compounds. These compounds must be decomposed/deperoxidized in a specific step in order to obtain one or more oxidized products such as acids, diacids, alcohols and ketones.

One of the major industrial processes belonging to this group is the process for manufacturing diacids, more particularly adipic acid, by oxidation of cyclohexane to cyclohexyl hydroperoxide (CyOOH) and then decomposition (also called deperoxidation) of this peroxide into alcohol and/or ketone. The latter oxidized compounds are then converted into diacids, mainly adipic acid, via oxidation by nitric acid. Adipic acid is an important chemical intermediate used in the manufacture of many polymers, such as polyamides and polyurethanes for example. This compound may also have many other applications.

Following the oxidation of cyclohexane to CyOOH, after optionally removing the unreacted cyclohexane and washing the reaction medium with water in order to recover and extract certain by-products formed, the CyOOH is then decomposed/deperoxidized to cyclohexanone and cyclohexanol, in the presence of a catalyst.

The decomposition of organic peroxides and especially of CyOOH, can firstly be carried out by homogeneous catalysis; that is to say in the presence of a catalyst dissolved in the reaction mixture.

Such catalysts comprise, as the main catalytic element, chromium, preferably in the form of chromium compounds of VI valency such as, for example, a chromic acid ester. Such chromium catalysts are described in U.S. Pat. No. 3,927,105 and in US 2012/0310012 A1. Among them, di-tert-butyl chromate is one of the preferred chromium catalysts for the decomposition of CyOOH.

Such catalysts being based on chromium with VI valency and therefore CMR (Carcinogenic, Mutagenic and Reprotoxic) and further being homogeneous catalysts, their use implies to put safety precautions in place and also to deal with continuous production of toxic effluents.

Other homogeneous catalysts which have been proposed are osmium-based catalysts. They present however the disadvantages of being constituted of metal presenting availability problems and of presenting toxicity problems. Ruthenium-base catalysts were also proposed but these, while being active, are not economically interesting compared to chromium-based catalysts.

More complex catalytic systems have also been recommended, such as complexes between a metal and a ligand among porphyrin, phthalocyanine, isoindoline, triphenylphosphine, quaternary ammonium, phosphonium or pyridinium. However, such systems do not show industrial application interest.

Finally, the above-mentioned catalysts being homogeneous catalysts, they also present the disadvantage of being more difficult to separate from the media and to be recycled.

It has therefore been proposed to decompose the organic peroxides by means of heterogeneous catalysts; that is to say in the presence of a catalyst not dissolved in the reaction mixture.

Catalysts qualified as heterogeneous catalysts based on ruthenium, gold, silver or chromium have been described for such reaction. However, some of them present the disadvantage of leading to metal leaching. Therefore, the catalysis becomes homogenous limiting the interest of these systems. Some of these catalysts present also the disadvantage of being expansive.

It therefore remains a need in finding a catalyst which allows the manufacture of at least one alcohol and/or at least one ketone starting from an organic peroxide compound without presenting the drawbacks recited above. Applicant has found in this context a new type of catalytic system for such reaction which is economically beneficial. Such heterogeneous catalytic system also presents virtually no metal leaching and can be recovered and recycled with consequently no production of toxic chromium VI containing effluents.

The present invention relates therefore to a process for the manufacture of at least one alcohol and/or at least one ketone, which comprises a step during which at least one organic peroxide compound is put into contact with at least one catalyst responding to formula I $$CrN_xO_y \qquad \text{Formula I}$$

in which x is a number varying from 0.10 to 1.00 and y is a number varying from 0.00 to 1.50, in order to produce the at least one alcohol and/or at least one ketone.

By the wording "at least one organic peroxide compound", it is meant, for the purpose of the present invention, that one or more than one organic peroxide compound can be put into contact with the catalyst(s) according to the invention. Preferably, (only) one organic peroxide compound is put into contact with the catalyst(s) according to the invention.

By the wording "at least one catalyst responding to formula I", it is meant, for the purpose of the present invention, that the organic peroxide compound(s) is(are) put into contact with one or more than one catalyst responding to formula I.

By the wording "at least one alcohol and/or at least one ketone", it is meant, for the purpose of the present invention, one or more than one alcohol and/or one or more than one ketone. More than one alcohol and/or more than one ketone can be obtained when more than one organic peroxide compound is put into contact with the catalyst(s) according to the invention. Preferably, the process according to the invention is a process for the manufacture of (only) one alcohol and/or (only) one ketone. More preferably, the process according to the invention is a process for the manufacture of (only) one alcohol and (only) one ketone.

The above-mentioned wordings will be used, indifferently in the singular form or in the plural form, in the text here after.

The catalyst used in the process according to the invention responds to formula I $$CrN_xO_y \qquad \text{Formula I}$$

in which x is a number varying from 0.10 to 1.00 and y is a number varying from 0.00 to 1.50.

The formula I is to be understood, in the context of the present invention, as defining the formula of catalyst which comprises one (1) atom of chromium and compared to this atom of chromium, x atom(s) of nitrogen and y atom(s) of oxygen. This means that for example, the catalyst of formula I which is $CrN_{0.50}$ is the same catalyst as the one of formula $Cr_2N$.

In formula I, x is a number varying from 0.10 to 1.00, preferably from 0.20 to 1.00, more preferably from 0.30 to 1.00, most preferably from 0.40 to 1.00 and particularly most preferably from 0.50 to 1.00.

In formula I, y is a number varying from 0.00 to 1.50, preferably from 0.00 to 1.25, more preferably from 0.00 to 1.00 most preferably from 0.0 to 0.80 and particularly most preferably from 0.00 to 0.60.

In a preferred embodiment of formula I, x is a number varying from 0.50 to 1.00 and y is a number varying from 0.00 to 1.00.

In a more preferred embodiment of formula I, x is a number varying from 0.50 to 1.00 and y is a number varying from 0.00 to 0.60.

The catalyst used in the process according to the invention is particularly preferably chosen among
chromium nitrides of formula $CrN_x$ in which x is a number varying from 0.10 to 1.00 preferably from 0.20 to 1.00 more preferably from 0.30 to 1.00 most preferably from 0.40 to 1.00 and particularly most preferably from 0.50 to 1.00;
mixtures comprising such chromium nitrides;
chromium oxynitrides of formula $CrN_xO_y$ in which x is a number varying from 0.10 to 1.00 preferably from 0.20 to 1.00 more preferably from 0.30 to 1.00 most preferably from 0.40 to 1.00 and particularly most preferably from 0.50 to 1.00 and y is a number varying from 0.10 to 1.50, preferably from 0.10 to 1.23, more preferably from 0.20 to 1.00 most preferably from 0.30 to 0.80 and particularly most preferably from 0.40 to 0.60; and
mixtures comprising such oxynitrides.

The catalyst used in the process according to the invention is more particularly preferably chosen among
chromium nitrides of formula $CrN_x$ in which x is a number varying from 0.50 to 1.00;
mixtures comprising such chromium nitrides;
chromium oxynitrides of formula $CrN_xO_y$ in which x is a number varying from 0.50 to 1.00 and y is a number varying from 0.40 to 0.60; and
mixtures of such oxynitrides.

The catalyst used in the process according to the invention is most particularly preferably chosen among chromium nitride responding to formula CrN, mixture of chromium nitride responding to formula CrN and of chromium heminitride responding to formula $Cr_2N_x$ and chromium oxynitride responding to formula $CrN_{0.73}O_{0.48}$.

Preferred chromium nitride of formula CrN is high surface chromium nitride (CrN(hs)).

By the wording "organic peroxide compound", it is meant, for the purpose of the invention, an organic compound the formula of which comprises the function —O—O—.

The organic peroxide compound is advantageously a hydroperoxide compound responding to formula II R—O—O—H      Formula II in which R is a hydrocarbon group comprising from 1 to 15, preferably from 2 to 12, more preferably from 3 to 10, most preferably from 4 to 9, carbon atoms, advantageously selected from alkyl groups and aryl groups.

The hydroperoxide compound is preferably chosen in the group consisting of tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e. tetrahydronaphtalene) hydroperoxide, isobutylbenzene hydroperoxide and ethylnaphthalene hydroperoxide.

The hydroperoxide compound is more preferably chosen in the group consisting of tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e. tetrahydronaphtalene) hydroperoxide and isobutylbenzene hydroperoxide.

The hydroperoxide compound is most preferably chosen in the group consisting of tert-butyl hydroperoxide, tert-amyl hydroperoxide, cumene hydroperoxide, ethylbenzene hydroperoxide, cyclohexyl hydroperoxide and methylcyclohexyl hydroperoxide.

The hydroperoxide compound is particularly most preferably chosen in the group consisting of tert-butyl hydroperoxide, tert-amyl hydroperoxide, cumene hydroperoxide and cyclohexyl hydroperoxide.

Very interesting results are obtained with a hydroperoxide compound chosen in the group consisting of tert-butyl hydroperoxide, cumene hydroperoxide and cyclohexyl hydroperoxide.

In a particularly preferred alternative of the process according to the invention, the hydroperoxide compound is cyclohexyl hydroperoxide. In this particularly preferred alternative, the at least one alcohol and/or at least one ketone is therefore cyclohexanol and/or cyclohexanone.

The organic peroxide compound is advantageously used in a solution in an alkane. Any alkane can be used with a preference for cyclohexane. The concentration of the organic peroxide compound in the solution in an alkane, preferably in cyclohexane, is advantageous comprised between 0.1 wt % and 50 wt %, preferably between 2 wt % and 10 wt % and more preferably between 2.5 wt % and 8 wt %.

The amount of catalyst involved may vary widely, especially depending on the conditions under which the process is carried out. In general, the amount of catalyst expressed as a molar percentage of active metal with respect to the organic peroxide compound to be decomposed represents from 0.0001% to 10000% and preferably from 0.01% to 100%. The amount of catalyst with respect to the organic peroxide compound may however be much higher, in particular within the context of a continuous operation of the process.

According to a preferred mode of the particularly preferred alternative, the cyclohexyl hydroperoxide is generated by reaction of cyclohexane with an oxygen generator.

Oxygen generator can be pure molecular oxygen, air, oxygen-enriched air, oxygen-depleted air or, alternatively, oxygen diluted with an inert gas. Oxygen generator is preferably molecular oxygen or air. Oxygen generator is more preferably air.

In the practice of the invention, the catalyst can be contacted with an organic peroxide compound by formulation into a catalyst bed, which is arranged to provide intimate contact between the catalyst and the organic peroxide compound. Alternatively, catalyst can be slurried with the organic peroxide compound using techniques known in the art.

The process according to the invention can be a batch or a continuous process and is preferably a continuous process.

The process can be performed under a wide variety of conditions, as will be apparent to persons of ordinary skill.

The contact between the peroxide and the catalyst is performed advantageously at a temperature from 20° C. to 200° C., preferably from 50° C. to 180° C. and more preferably from 70° C. to 120° C.

The contact between the peroxide and the catalyst is performed advantageously at a pressure from 0.1 MPa (1 bar) to 1.5 MPa (15 bar), preferably from 0.1 MPa (1 bar) to 1 MPa (10 bar) and more preferably from 0.1 MPa (1 bar) to 0.3 MPa (3 bar).

Residence time generally varies in inverse relation to reaction temperature, and typically is comprised from 10 to 180 minutes.

At the end of the reaction, the compound of interest is advantageously purified by well-known methods of the technical field, such as distillation.

EXAMPLES

The following examples are intended to illustrate the invention without however limiting the scope thereof.

Analysis

Iodometry

Cyclohexyl hydroperoxide (CyOOH) was quantified by iodometry which consisted in reacting CyOOH with potassium iodide to yield cyclohexanol and iodine. The amount of iodine formed was estimated by potentiometry by reaction of iodine with sodium thiosulfate ($Na_2S_2O_3$).

About 1 g of a solution containing CyOOH was weighed in an Erlenmeyer flask. Then, 20 mL of 80% acetic acid, about 1 g of sodium hydrogenocarbonate ($NaHCO_3$) and about 1 g of potassium iodide were introduced. $NaHCO_3$ is a weak base and reacted with acetic acid to produce carbon dioxide, so that oxygen was pushed away. Indeed, the presence of oxygen would induce error on the evaluation of the CyOOH quantity.

After mixing, the Erlenmeyer flask was stored 20 minutes in the dark. The Erlenmayer flask was washed with distilled water and acetonitrile (which avoids the formation of foam). The solution was dosed with a solution of $Na_2S_2O_3$ (0.1 N) thanks to a potentiometer equipped with a Pt probe (ref 60451100 Metrohm).

Gas Chromatography (GC)

The reaction mixture containing cyclohexane, CyOOH, cyclohexanol, cyclohexanone and small amounts of other byproducts (carboxylic acids . . . ) were quantified by GC using a specific polar column (Permabond FFAP length 20 m, film thickness 0.10 μm) after calibration with different CyOOH solutions of known concentrations established by iodometry.

Elemental Analyses (EA) were performed by Inductively Coupled Plasma-Mass Spectroscopy (ICP-MS) or by Atomic Absorption Spectroscopy (AAS).

Dinitrogen physisorption for BET area quantification was performed on a Micromeritics Tristar Surface Area and Porosity Analyser at 77 K. BET analyses allowed to determine the surface area of the catalysts.

Materials

Purified Cyclohexyl Hydroperoxide (CyOOH) Solution

CyOOH was extracted from a cyclohexane oxidate resulting from the thermal oxidation of cyclohexane by oxygen The oxidate was extracted three times with 1 M NaOH (Merck) and the water phase was then neutralized with a chilled aqueous 4 M HCl (Merck, pro analysi, at least 99 wt %) solution until slightly acidic. The water phase was subsequently extracted 3 times with cyclohexane (Sigma Aldrich, >99%) and dried over $Na_2SO_4$ or $MgSO_4$ (Merck). Finally, 1% mol biphenyl (Acros, 99%) was added to the filtered solution as an internal standard for GC analysis and the solution was diluted with cyclohexane to concentrations ranging from 2-5.5 wt % CyOOH.

Tert-Butyl Hydroperoxide (tBuOOH)

A 70% tBuOOH/water solution was purchased from Aldrich. The solution was extracted with cyclohexane to get a tBuOOH/cyclohexane solution. The title was adjusted to 4.9 wt % after titration by iodometry.

Cumene Hydroperoxide

Cumene hydroperoxide 80% was purchased from Aldrich and diluted in cyclohexane to get a concentration of cumene hydroperoxide of 3.3 wt % checked by iodometry.

Catalysts According to the Invention

High-Surface Chromium Nitride (CrN (Hs))

CrN (hs) was prepared as described below and was characterized by a surface area of 20 $m^2g^{-1}$. The data resulting from EA were Cr 74.10 wt % and N 20.02 wt %.

First, precipitated chromium oxide ($Cr_2O_3$) was prepared from $Cr(NO_3)_3.9\ H_2O$. A 0.5 M ethanol solution of $Cr(NO_3)_3.9\ H_2O$ (1.8 g in 9.2 mL) was dropped slowly by means of a burette in a magnetically stirred Erlenmeyer flask containing 5 mL of 25% aqueous ammonia solution (Aldrich), which helped to keep the pH between 9-10, and drops of the same solution were added to maintain the values within the aforementioned interval. Right after the addition, a dark-grey precipitate formed and stiffing was kept for 90 min more. The solid was vacuum-filtered and washed repeatedly with ethanol and water (30 mL, three times each). The filter cake was taken to the oven and kept at 80° C. during 24 h. The resulting green solid of $Cr_2O_3$ was calcined under dry, stagnant air at 450° C. for 2 h more, using a 5 $C \cdot min^{-1}$ ramp.

The synthesis of CrN (hs) from precipitated $Cr_2O_3$ was performed as follows.

In a crucible enabled with a cap, 1.37 g of $Cr_2O_3$ were first dissolved in 10 mL of demineralized water with the help of a stiffing bar. When the solid was dissolved, 500 mg of mesoporous silica SBA-15 were added and the stirring (low) was kept overnight. Afterwards, the suspension was heated open in the oven at 90° C. and 0.5° $C.min^{-1}$ ramp during more than 10 hours. The resulting material was calcined at 500° C. during 18 h and then treated in a tubular oven with a stream of pure ammonia (99.98%, Linde, 60-100 $mL \cdot min^{-1}$), first with a ramp of 2° C. per min, up to 950° C., with a dwelling time of 10 h. Passed this time, the temperature was decreased at 0.5° C. per min down to 700° C., always under running ammonia. The resulting black solid was treated with a 18% NaOH solution during 24 h to remove all the silica template. Finally, the resulting suspension was centrifuged and washed several times with ethanol and water, centrifuged every time to remove the washing solvents. A total of 8 washing/centrifuge treatments were done. Finally, the solid was dried at 120° C. overnight under stagnant air and characterized by EA. 590 mg were isolated.

Chromium Oxynitride ($CrN_{0.73}O_{0.48}$)

$CrN_{0.73}O_{0.48}$ was prepared as follows and was characterized by a surface area of 7.09 $m^2g^{-1}$.

A fraction of the $Cr_2O_3$ obtained above (1 g) was placed in an alumina crucible and set to react in a tubular oven under a flow of anhydrous ammonia (99.98%, Linde, 60-100 $mLmin^{-1}$) at 800° C. for 8 h, using a ramp of 6 $C \cdot min^{-1}$. Passed this time, the oven was switched off and the flux of ammonia maintained until the tube containing the solid reached ambient temperature. Afterwards, the oven was flushed with nitrogen and the resulting solid isolated and stored in a flask. Results from EA were Cr 74.43 wt %, N 14.61 wt %, O 10.96 wt % (O obtained by subtraction); (% mol) Cr 45.30, N 33.03, O 21.68; proposed stoichiometry, assuming all the solid is in the form of the oxynitride, $CrN_{0.73}O_{0.48}$.

Chromium Nitride and Chromium Heminitride Mixture ($CrN/Cr_2N$)

$CrN/Cr_2N$, which is a mixture of CrN and $Cr_2N$, used in examples 1 and 2 was purchased from Aldrich and used as received. It was characterized by 350 mesh, a surface area <1 $m^2g^{-1}$ and the results obtained from EA were Cr 83.42 wt % and N 16.23 wt %. This composition corresponds to a mixture of 38 wt % $Cr_2N$ and 62 wt % CrN.

$CrN/Cr_2N$, which is a mixture of CrN and $Cr_2N$, used in examples 13 to 19 was supplied by Alfa Aesar and used as received.

Other Catalysts $CrO_2(OtBu)_2$ $CrO_2(OtBu)_2$ was prepared according to the procedure described in US 2012/0310012 A1.

Chromium Aluminophosphates (CrAPO-5)

CrAPO-5 was prepared according to the procedure detailed here after (based on U.S. Pat. No. 4,559,919). Chromium nitrate [$Cr(NO_3)_3.9H_2O$, 1.6 g] was dissolved in demineralized water (10 mL). Hydrochloric acid (0.6 mL, conc.) was added to the solution, followed by acetic acid (0.68 g, glacial). The mixture was stirred for a few minutes then phosphoric acid (5.52 mL, 85 wt %) was added drop wise. The homogenized mixture was added to previously hydrolyzed slurry of alumina (5.26 g, pseudoboehmite, Catapal B) in water (10 mL). After one hour of stirring, the reaction mixture was cooled to 0° C. and triethyl amine was added drop wise. Stirring was continued for two more hours. The resulting pale-purple gel was charged in a Teflon® autoclave and heated at 175° C. under autogenous pressure during 24 h. The solid was recovered, filtered and washed several times with distilled water. After drying, the resulting green cake was calcined at 500° C. in a static oven during 16 h. The calcined solid was set to exchange with a sodium chloride solution (400 mL, 0.1 mol $L^{-1}$, Na/Cr >100) for periods of 8 h. Washing was repeated until no Cr leached was detected by AAS (<0.1 ppm) then washed with distilled water and recalcined at 500° C. under static conditions. X-ray of the solid showed the formation of CrAPO-5 in the form of microcrystalline material. Results of EA on the obtained catalyst were: Cr 0.77 wt %.

Chromium Supported on a Nitridised Carbon Polymer (Cr/Pdap) (Pdap=Polydiaminopyridine)

As the initial step, 5.45 g of 2,6-diaminopyridine and 1 g of sodium hydroxide were dissolved in 400 ml of distilled water, followed by the addition of 17.1 g of ammonium persulfate and 100 ml of distilled water. The resultant mixture was agitated for several minutes and the polymerization reaction was carried out without agitation at 10° C. for 12 h. Black solid was collected by centrifugation and rinsed with distilled water three times to obtained pdap particles. They were then vacuum-dried at 70° C.

To synthesize Cr/pdap catalyst, pdap and chromium (III) nitrate hydrate ($Cr(NO_3)_3$ $9H_2O$) were mixed in a solution of ethanol and water to form a precursor composite. Typically, 5.45 g pdap and 1 g $Cr(NO_3)_3$ $9H_2O$ were suspended in 150 ml of water/ethanol (1/1 v/v). After mixing them for 1 h in an ultrasonic probe system and agitating the solution for additional 2 h at 60° C., the solution was evaporated under vacuum at 60° C. The remaining dry powder was grinded using a quartz mortar.

Cr/pdap powder was put into a tubular furnace and pyrolyzed in the presence of ammonia gas for 1 or 1.5 h. A quartz tube was used for pyrolysis under a temperature program (0-200° C., 1 h; 200° C., 1 h; 200-700° C., 0.75 h; 700° C., 1.5 h; 700-0° C., 2 h). Heat-treated product was ultrasonically leached in concentrated hydrochloride (HCl) acid for 8 h to remove unstable and inactive metal species from the catalysts. The leached sample was washed in water three times. Finally, the catalyst was collected by filtration and dried at 60° C.

Cobalt Supported on a Nitridised Carbon Polymer (Co/Pdap) (Pdap=Polydiaminopyridine)

The catalyst was prepared in an identical way as Cr/pdap using 3.62 g $CoNO_3$ $6H_2O$ instead of 1 g of $Cr(NO_3)_3$ $9H_2O$.

Chromium Carbide ($Cr_3C_2$)

$Cr_3C_2$ was purchased from ABCR and used as received. It was characterized by 350 mesh, a surface area <1 $m^2 \cdot g^{-1}$ and the results obtained from EA were Cr 80.26 wt % and C 12.23 wt %.

Tungsten Carbide (WC)

WC was purchased from ABCR and used as received.

Vanadium Nitride (VN)

VN was purchased from ABCR and used as received.

Hexagonal Boron Nitride (h-BN)

h-BN was purchased from Aldrich and used as received.

Tantalum Nitride (TaN)

TaN was purchased from Aldrich and used as received.

Titanium Nitride (TiN)

TiN was purchased from Aldrich and used as received.

Examples 1 to 12

The decomposition of CyOOH (called deperoxidation) into cyclohexanol and cyclohexanone was carried out in a 50 mL round-bottom flask equipped with a Dean-Stark trap filled with cyclohexane, a reflux condenser and an arm for collecting aliquots. A CyOOH solution was placed in the round flask and heated to reflux at 80° C. Samples were taken from the flask during reaction using tip filters (HDPE, 0.45 µm) to isolate the aliquots and the reaction was tracked by GC.

In the case of hot filtration experiments, the reaction was typically stopped after 30-40% conversion and filtered in hot using a fast-filtration funnel using a large plug of cotton tightly pressed through the stem (filtration took around one minute). The recovered filtrate was set to resume the reaction without the solid catalyst and the reaction was tracked by GC again.

Example 1 (According to the Invention)

40 g of a CyOOH purified solution (~4.5 wt % in cyclohexane) and 0.125 g of $CrN/Cr_2N$ were heated in an oil bath to reflux.

To study the degree of leaching at different stages, the reaction medium was hot-filtered at different conversions and the filtrates were analyzed by AAS. At low conversion (10%), leaching was barely detectable (chromium measured in solution <0.1 mg/$L^{-1}$). The filtered solution was heated and we observed that reaction was stopped meaning the quantity of soluble chromium in solution was low.

At higher conversion (30% and 75%), the concentration of chromium measured in solution was still very low (0.3 mg·$L^{-1}$). Heating the filtered solution showed that CyOOH was slowly converted to cyclohexanol and cyclohexanone meaning small amount of chromium has leached in solution. However, the reaction rate obtained with the filtered solution was lower than the rate obtained with initial $CrN/Cr_2N$. This observation led us to the conclusion that observed activity in $CrN/Cr_2N$ test was only partly due to leached chromium but also to heterogeneous CrN/Cr$_2$N catalyst. Hence, CrN/Cr$_2$N had a strong heterogeneous contribution.

Example 2 (According to the Invention)

40 g of a CyOOH purified solution (~5.5 wt % in cyclohexane) and 1 g of CrN/Cr$_2$N were heated in an oil bath to reflux. The rate constant observed was 0.017 min$^{-1}$.

Another run was made under the same conditions except that the medium was hot filtered after 30 minutes of reaction at 30% conversion. The filtered solution was heated to reflux. It was observed that reaction continued after filtering the medium meaning some chromium had leached from the catalyst. However, the reaction rate constant after filtration was 0.0064 min$^{-1}$ and was thus much lower than with initial CrN/Cr$_2$N (0.017 min$^{-1}$). As a consequence, observed activity in CrN/Cr$_2$N test was partly due to leached chromium but also to heterogeneous CrN/Cr$_2$N catalysts. Hence, CrN/Cr$_2$N has a heterogeneous contribution.

Example 3 (According to the Invention)

40 g of a CyOOH purified solution (~5.5 wt % in cyclohexane) and 0.05 g of CrN (hs) were heated in an oil bath to reflux. After 30 minutes of reaction and 25% conversion, the medium was filtered and the solution without solid catalyst was heated to reflux. The reaction was tracked by GC before and after filtration. It was observed that reaction continued after filtering the medium meaning some chromium has leached from the catalyst. However reaction rate constant decreased from 0.01 min$^{-1}$ before filtration to 0.005 min$^{-1}$ after filtration. As a consequence, observed activity in CrN (hs) test was partly due to leached chromium but also to heterogeneous CrN (hs) catalysts. Hence, CrN (hs) has a heterogeneous contribution.

Example 4 (Comparative Example)

40 g of a CyOOH purified solution (5.5 wt % in cyclohexane) and 0.7 g of CrAPO5 were heated in an oil bath to reflux. The reaction was tracked by GC and the rate constant observed was 0.017 min$^{-1}$.

Another run was made under the same conditions except that the medium was hot filtered after 30 minutes of reaction and 40% conversion. The filtered solution was heated to reflux. It was observed that reaction continued after filtering the medium meaning some chromium had leached from the catalyst. The reaction rate constant after filtration was 0.014 min$^{-1}$ which is comparable to the rate obtained when using CrAPO5. It means that catalytic activity was virtually all homogeneous.

Example 5 (Comparative Example)

The following example relates to the use of Cr/pdap. The reaction was performed using the same procedure as example 4.

40 g of a CyOOH purified solution (5.3 wt % in cyclohexane) and 100 mg of Cr/pdap were heated in an oil bath to reflux. After hot filtration (50 min, 41% conversion), the reaction rate did not change significantly, suggesting the catalytic reaction was virtually all homogeneous contrary to what was observed in example 1 with CrN/Cr$_2$N.

Example 6 (Comparative Example)

40 g of a CyOOH purified solution (ca. 5.5 wt % in cyclohexane) and 1 g of Cr$_3$C$_2$ were heated in an oil bath to reflux. Upon hot filtration (58 min, 39% conversion), no changes in the reaction rate were observed, which strongly suggested the whole reaction took place in the homogeneous phase contrary to what was observed in example 1 with CrN/Cr$_2$N.

Example 7 (Comparative Example)

40 g of a CyOOH purified solution (ca. 5.5 wt % in cyclohexane) and 1 g of WC were heated in an oil bath to reflux. Most notably, upon hot filtration (30 min, 3.26% conversion), no changes in the reaction rate were observed, which strongly suggested the whole reaction took place in the homogeneous phase contrary to what was observed in example 1 with CrN/Cr$_2$N.

Example 8 (Comparative Example)

40 g of a CyOOH purified solution (ca. 2.5 wt % in cyclohexane) and 0.130 g of VN were heated in an oil bath to reflux. A reaction took place but the reactivity of VN at ambient temperature and obvious coloration of the filtrate after the reaction were a clear indication of the homogeneous nature of VN.

Example 9 (Comparative Example)

40 g of a CyOOH purified solution (ca. 2.5 wt % in cyclohexane) were heated in an oil bath to reflux. When the mixture was boiling, 130 mg of h-BN were added. No reaction took place.

Example 10 (Comparative Example)

Example 9 was reproduced replacing the 130 mg of h-BN by the same quantity of TaN no reaction took place, Example 11 (Comparative Example)

Example 9 was reproduced replacing the 130 mg of h-BN by 50 mg of TiN. No reaction took place.

Example 12 (Comparative Example)

The following example relates to the use of Co/pdap.
The catalytic test was performed as described in example 5 replacing the 100 mg of Cr/pdap by 50 mg of Co/pdap. No reaction was observed.

Example 13 (According to the Invention)

To ascertain the heterogeneous nature of the catalysts according to the invention and study the stability of these catalysts, a fixed bed test was undertaken. The reactor was a liquid full plug flow glass reactor of 0.5 cm internal diameter. The feed consisted of a 4.5 wt % CyOOH solution. In order to increase particle size of the catalyst, 1.62 g of CrN/Cr$_2$N were mixed with 0.19 g of silica and pressed to pellets. Then the catalyst was crushed and sieved between 450 and 560 μm. The CyOOH flow was fed over the catalyst at 0.3 mL/min at 70° C. This reaction enabled to obtain 20% of conversion. The conversion was stable over a period of 6 h without loss of activity, which confirms that chromium did not leach from catalyst and that CrN/Cr$_2$N had a heterogeneous behavior.

Example 14 (According to the Invention)

To ascertain the heterogeneous nature of the catalysts according to the invention and study the stability of these catalysts at higher conversion, a fixed bed test with a higher amount of catalyst was undertaken. The reactor was a liquid full plug flow glass reactor of 0.5 cm internal diameter. The feed consisted of a 4.7 wt % CyOOH solution. In order to increase particle size of the catalyst, 15 g of CrN/Cr$_2$N were mixed with 2.65 g of silica and pressed to pellets and prepared as in example 13. The CyOOH flow was fed over the catalyst at 0.3 mL/min at 80° C. We observed an initial conversion of 80% which decreased with time to 14% after 169 h of reaction and stabilized to this value during 46 h. The initial decrease of activity is due to the loss of chromium by leaching. Stabilization after 169 h shows that leaching is then lowered.

Then, after 217 h of reaction, the CyOOH flowrate was reduced to 0.15 mL/min in order to increase conversion. The conversion rose to 28% and then slightly decreased to 25% after 436 h test and stabilized to this value during 24 h. The stabilization of activity confirms that CrN/Cr$_2$N has an heterogeneous behavior and that leaching is very low.

Example 15 (According to the Invention)

We added a second liquid full plug flow glass reactor (0.5 cm internal diameter) at the outlet of the reactor described in example 14. The second reactor was filled with 15.6 g of CrN/Cr$_2$N mixed with 2.76 g of silica (and pressed to pellets and prepared as in example 13), whereas used catalyst remained unchanged in the first reactor. The feed consisted of a 4.7 wt % CyOOH solution flowing at 0.15 mL/min and passing through the 2 fixed bed reactors heated at 80° C. The initial conversion was 90% which decreased to 50% after 460 h. The conversion then remained unchanged at 50% during 240 h. The initial decrease of activity is ascribed to initial leaching of the new catalyst. Stabilization at 50% conversion means leaching is very low confirming the heterogeneous nature of CrN/Cr$_2$N.

Example 16 (According to the Invention)

The mixture obtained from example 15 after passing through 2 fixed bed reactors has been recycled to the inlet of the first reactor. Under identical conditions as described in example 15, the global conversion reached 70% and was stable at this value during 117 h, thus confirming the heterogeneous behavior of CrN/Cr$_2$N.

Examples 17 to 19 (According to the Invention)

The examples 17 to 19 showed that CrN/Cr$_2$N can be used in the decomposition of different organic peroxides into corresponding alcohol and ketone, even if conversion is low for some of them.

Example 17

3.1 g of a 4.9% CyOOH solution in cyclohexane were added in a 10 mL tube equipped with a magnetic stirrer. Then 376 mg of CrN/Cr$_2$N were weighed and added to the reaction mixture. The medium was heated to reflux at 80° C. and remained at this temperature during 2 hours. After being cooled down to room temperature, the mixture was analyzed by iodometry. After that time, all CyOOH had reacted and the conversion was 100%.

Example 18

Example 17 was reproduced with 3.2 g of the 4.9 wt % t-butyl hydroperoxide solution in cyclohexane and 378 mg of the same catalyst. After the 2 hours, 3.32 wt % of t-butyl hydroperoxide still remained in the medium and the conversion was 32%.

Example 19

Example 17 was reproduced with 3.2 g of the 3.3 wt % cumene hydroperoxide solution in cyclohexane and 366 mg of the same catalyst. After the 2 hours, 3.1 wt % of cumene hydroperoxide still remained in the medium and the conversion was 6%.

The invention claimed is:

1. A process for the manufacture of at least one alcohol and/or at least one ketone, comprising contacting at least one organic peroxide compound with at least one catalyst responding to formula I:

CrN$_x$O$_y$ (formula I)

wherein x is a number from 0.10 to 1.00 and y is a number from 0.00 to 1.50.

2. The process according to claim 1, wherein x is a number from 0.50 to 1.00 and y is a number from 0.00 to 1.00.

3. The process according to claim 1, wherein x is a number from 0.50 to 1.00 and y is a number from 0.00 to 0.60.

4. The process according to claim 1, wherein the catalyst is chosen among:
chromium nitrides of formula CrN$_x$ in which x is a number from 0.50 to 1.00;
mixtures comprising such chromium nitrides;
chromium oxynitrides of formula CrN$_x$O$_y$ in which x is a number from 0.50 to 1.00 and y is a number from 0.40 to 0.60; and
mixtures comprising such oxynitrides.

5. The process according to claim 1, wherein the organic peroxide compound is a hydroperoxide compound responding to formula II:

R—O—O—H (formula II)

in which R is a hydrocarbon group comprising from 1 to 15 carbon atoms.

6. The process according to claim 1, wherein the organic peroxide compound is a hydroperoxide compound responding to formula II:

R—O—O—H (formula II)

in which R is a hydrocarbon group comprising from 4 to 9 carbon atoms.

7. The process according to claim 1, wherein the hydroperoxide compound is chosen in the group consisting of tert-butyl hydroperoxide, tert-amyl hydroperoxide, cumene hydroperoxide, ethylbenzene hydroperoxide, cyclohexyl hydroperoxide and methylcyclohexyl hydroperoxide.

8. The process according to claim 1, wherein the hydroperoxide compound is chosen in the group consisting of tert-butyl hydroperoxide, cumene hydroperoxide and cyclohexyl hydroperoxide.

9. The process according to claim 1, wherein the hydroperoxide compound is cyclohexyl hydroperoxide.

10. The process according to claim 9, wherein the at least one alcohol and/or at least one ketone is cyclohexanol and/or cyclohexanone.

11. The process according to claim 9, wherein the cyclohexyl hydroperoxide is generated by reaction of a cyclohexane with an oxygen generator.

12. The process according to claim 11, wherein the oxygen generator is air.

13. The process according to claim 1, wherein the contact between the peroxide and the catalyst is performed at a temperature from 20° C. to 200° C.

14. The process according to claim 1, wherein the contact between the peroxide and the catalyst is performed at a pressure from 0.1 MPa to 1.5 MPa.

\* \* \* \* \*